US010455837B2

(12) United States Patent
Zhao et al.

(10) Patent No.: US 10,455,837 B2
(45) Date of Patent: Oct. 29, 2019

(54) COMPLEXES OF CLOQUINTOCET AND AMINE-CONTAINING POLYMERS OR OLIGOMERS

(71) Applicant: DOW AGROSCIENCES LLC, Indianapolis, IN (US)

(72) Inventors: Min Zhao, Carmel, IN (US); Lei Liu, Carmel, IN (US); David Ouse, Indianapolis, IN (US); James Gifford, Lebanon, IN (US)

(73) Assignee: Dow ArgoSciences LLC, Indianapolis, IN (US)

( * ) Notice: Subject to any disclaimer, the term of this patent is extended or adjusted under 35 U.S.C. 154(b) by 0 days.

(21) Appl. No.: 15/246,604

(22) Filed: Aug. 25, 2016

(65) Prior Publication Data

US 2017/0055530 A1 Mar. 2, 2017

Related U.S. Application Data

(60) Provisional application No. 62/210,115, filed on Aug. 26, 2015.

(51) Int. Cl.
*A01N 43/42* (2006.01)
*A01N 43/90* (2006.01)
*A01N 25/32* (2006.01)

(52) U.S. Cl.
CPC ............. *A01N 43/42* (2013.01); *A01N 25/32* (2013.01); *A01N 43/90* (2013.01)

(58) Field of Classification Search
CPC combination set(s) only.
See application file for complete search history.

(56) References Cited

U.S. PATENT DOCUMENTS

| | | | |
|---|---|---|---|
| 5,527,524 A | 6/1996 | Tomalia et al. | |
| 6,121,200 A | 9/2000 | Berger et al. | |
| 7,314,849 B2 | 1/2008 | Balko et al. | |
| 7,432,227 B2 | 10/2008 | Balko et al. | |
| 9,204,643 B2 * | 12/2015 | Hopkins | A01N 43/42 |
| 9,591,857 B2 * | 3/2017 | Buysse | A01N 43/78 |
| 2002/0107149 A1 | 8/2002 | Volgas et al. | |
| 2002/0160916 A1 | 10/2002 | Volgas et al. | |
| 2006/0040828 A1 | 2/2006 | Mao et al. | |
| 2007/0149409 A1 | 6/2007 | Burnet et al. | |
| 2008/0085983 A1 | 4/2008 | Ahn et al. | |
| 2008/0182773 A1 | 7/2008 | Gauweiler et al. | |
| 2010/0062940 A1 | 3/2010 | Kolter et al. | |
| 2011/0275516 A1 | 11/2011 | Wu et al. | |
| 2012/0142532 A1 | 6/2012 | Wright et al. | |
| 2013/0045869 A1 | 2/2013 | Liu et al. | |
| 2014/0148510 A1 | 5/2014 | Pirotte et al. | |
| 2014/0179526 A1 * | 6/2014 | Hopkins | A01N 43/42 504/105 |
| 2014/0336051 A1 * | 11/2014 | Schnabel | A01N 43/50 504/130 |
| 2015/0210723 A1 * | 7/2015 | Xu | A01N 37/40 504/100 |

FOREIGN PATENT DOCUMENTS

| | | | | |
|---|---|---|---|---|
| EP | 0375624 A | 6/1990 | | |
| WO | 199104661 A2 | 4/1991 | | |
| WO | 9905914 A1 | 2/1999 | | |
| WO | 2005087007 A1 | 9/2005 | | |
| WO | 200706472 | 1/2008 | | |
| WO | 2008069826 A1 | 6/2008 | | |
| WO | 2009076349 A2 | 6/2009 | | |
| WO | 2009141367 A2 | 11/2009 | | |
| WO | 2011039172 A2 | 4/2011 | | |
| WO | 2011040956 A1 | 4/2011 | | |
| WO | WO 2011039172 A2 * | 4/2011 | ............. | A01N 37/40 |
| WO | 2012027349 A1 | 3/2012 | | |
| WO | 2012059494 A1 | 5/2012 | | |
| WO | 2012076567 A2 | 6/2012 | | |
| WO | 2013025758 A1 | 2/2013 | | |
| WO | 2013189773 A1 | 12/2013 | | |

OTHER PUBLICATIONS

Chitosan—Sigma-Aldrich.*
Lupasol® types technical information.*
Lupasol® types technical information (Year: 2017).*
Clamme et al., "Monitoring of the formation and dissociation of polyethyleneimine/DNA complexes by two photon fluorescence correlation spectroscopy", Biophys J 84: 1960-1968 (2003) (Year: 2003).*
Lupasol® types technical information (Sep. 2010) (Year: 2010).*
International Search Report and Written Opinion issued for International Application No. PCT/US2016/048526, dated Nov. 3, 2016.
Supplementary Search Report issued for related European Application EP12823900, dated Mar. 3, 2015.
International Search Report and Written Opinion issued for International Application No. PCT/US2012/050871, dated Oct. 16, 2012.
National Pesticide Information Center (NPIC), "Pesticide Formulations Topic Fact Sheet" <http://npic.orst.edu/factsheets/formulations.html>, Dec. 1999, p. 1-3.
Sigma-Aldrich®, "Poly(ethyleneimine) solution 50% (w/v) in H20", <http://www.sigmaaldrich.com/catalog/product/fluka/p3143?lang=en®io n=US>, copyright 2013, p. 1-2.
Akagane, et al., "Long-term protection. II. Effects of fungicidal polymers for long-term protection", Shikizai Kyokaishi , 45(9), 479-84 Coden: Skyoao; ISSN: 0010-180X, (1972).

* cited by examiner

*Primary Examiner* — John Pak
(74) *Attorney, Agent, or Firm* — Meunier Carlin & Curfman, LLC

(57) ABSTRACT

Safener complexes comprising cloquintocet acid, or a salt thereof, and an amine-containing polymer or oligomer as well as compositions comprising these safener complexes are provided. Also provided are methods of controlling undesirable vegetation in a crop, comprising applying to vegetation or an area adjacent to the vegetation or applying to soil or water to prevent the emergence or growth of the undesirable vegetation in a crop, a safened herbicidal composition comprising a herbicide and a safener complex comprising cloquintocet acid, or a salt thereof, and an amine-containing polymer or oligomer.

15 Claims, No Drawings

COMPLEXES OF CLOQUINTOCET AND AMINE-CONTAINING POLYMERS OR OLIGOMERS

CROSS-REFERENCE TO RELATED APPLICATIONS

This application claims the benefit of U.S. Provisional Application No. 62/210,115, filed Aug. 26, 2015, which is hereby incorporated herein by reference in its entirety.

FIELD OF THE DISCLOSURE

Safener complexes containing cloquintocet acid, or a salt thereof, and an amine-containing polymer or oligomer and methods of making and using thereof are described herein.

BACKGROUND

Many recurring problems in agriculture involve controlling the growth of undesirable vegetation that can, for instance, negatively affect the growth of desirable vegetation (e.g., crops). A variety of chemicals and chemical formulations (e.g., herbicides and herbicidal formulations) have been developed to control the growth of undesirable vegetation in crops. While such herbicides can be effective in controlling undesirable vegetation, in many cases, herbicides can also cause injury or even kill the crops to which they are applied. To mitigate this shortcoming, safeners can be provided with the herbicide to limit the phytotoxicity of the herbicidal active ingredient to the crop.

Cloquintocet-mexyl is a safener that can be used in conjunction with various herbicides to reduce phytotoxicity to crops. Though effective as a safener, the manufacture, storage, and use of cloquintocet-mexyl containing products can present challenges owing to its sensitivity to water and its low melting temperature (i.e., 61-69° C. for technical material). When products containing cloquintocet-mexyl are prepared, stored, or used in the presence of water, cloquintocet-mexyl can undergo hydrolysis to form cloquintocet acid, and/or form a needle-shaped, crystalline hydrate that can lead to clogged spray nozzles during spray applications and/or possibly increased levels of crop phytotoxicity.

Non-aqueous cloquintocet-mexyl formulations, such as oil dispersions and water dispersible granules, can also suffer from sensitivity to water during their preparation and storage since even small amounts of water picked up during processing and/or present in other components of the formulations can be problematic. In addition, the low melting temperature of cloquintocet-mexyl can make the manufacture and storage of solid formulations containing the safener, such as dispersible granules (DG), more difficult because temperatures above ambient temperature can cause agglomeration of the particles of cloquintocet-mexyl leading to problems with dispersion and suspensibility of the safener in cold water.

Because of the difficulties encountered with the preparation and use of cloquintocet-mexyl containing products, there is a need for improved safener compositions that are easy to prepare, flexible to use, and compatible with water.

SUMMARY

Provided herein are safener complexes. The safener complexes contain cloquintocet acid, or a salt thereof, and an amine-containing polymer or oligomer, such as a polyamine or oligoamine. The weight ratio of the cloquintocet acid, or a salt thereof, on an acid equivalent (AE) basis to the amine-containing polymer or oligomer in the complex is from about 1:2 to about 10:1 (e.g., 1:1 to 5:1). The safener complexes are easy to prepare, show less or no sensitivity to water, and have little or none of the stability challenges exhibited by cloquintocet-mexyl.

The amine-containing polymer or oligomer can be any suitable amine-containing polymer or oligomer. The amine-containing polymer or oligomer can have any suitable molecular weight. For example, the amine-containing polymer or oligomer can have an average molecular weight of from about 250 to 2,000,000 Daltons (e.g., from 500 to 10,000 Daltons). For example, the amine-containing polymer or oligomer can include or can be a polyethyleneimine. The polyethyleneimine can be a branched, spherical polyethyleneimine with a well-defined ratio of primary, secondary, and tertiary amine functional groups Also provided are compositions containing the safener complex, a pesticide (e.g., a fungicide, an insecticide, a herbicide, or a combination thereof), and optionally one or more agriculturally acceptable adjuvants or carriers. The compositions can be, for example, an emulsifiable concentrate (EC), an oil-in-water emulsion concentrate (EW), a suspension emulsion concentrate (SE), a solid composition such as a granule or powder, or an aqueous spray solution or mixture. In some embodiments, the pesticide is an acetolactate synthase (ALS) inhibitor, an acetyl CoA carboxylase (ACCase) inhibitor, a 4-aminopicolinic acid based herbicide, or a combination thereof. In certain embodiments, the pesticide is selected from clodinafop-propargyl, cyhalofop, fluazifop, flupyrsulfuron, haloxyfop, iodosulfuron, pinoxaden, pyrasulfotole, pyroxsulam, fenoxyprop, flucarbazone, flupyrsulfuron, halauxifen, halauxifen-methyl, mesosulfuron, quizalofop, thiencarbazone, an agriculturally acceptable salt or ester thereof, or a combination thereof.

Methods for preparing the safener complex are also disclosed. Methods for preparing the safener complex include reacting cloquintocet acid, or a salt thereof, with an amine-containing polymer or oligomer under conditions effective to form the safener complex. For example, cloquintocet acid, or a salt thereof, can be contacted with the amine-containing polymer or oligomer in a glycol ether solvent. In some embodiments, cloquintocet acid, or a salt thereof, can be contacted with the amine-containing polymer or oligomer at a temperature of from 10° C. to 75° C.

Further provided are methods of controlling undesirable vegetation in crops. Methods of controlling undesirable vegetation in crops include applying to the vegetation or an area adjacent to the vegetation, or applying to the soil to prevent the emergence of the vegetation a herbicidally effective amount of a composition containing a herbicide and a safener complex.

DETAILED DESCRIPTION

Disclosed herein are safener complexes. The safener complexes contain cloquintocet acid, or a salt thereof, and an amine-containing polymer or oligomer. "Amine-containing polymer or oligomer" as used herein refers to an oligomer or polymer containing a plurality (e.g., greater than one) of amine groups. The amine groups can be primary, secondary, tertiary, or quaternary amines or combinations thereof.

Cloquintocet acid (CQC; ((5-chloroquinolin-8-yl)oxy) acetic acid) is a quinoline compound that has the following chemical structure.

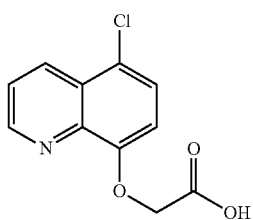 [SMILES: O=C(O)COc1ccc(Cl)c2cccnc12]

Cloquintocet acid (often provided in the form of an agriculturally acceptable ester of cloquintocet acid, e.g., cloquintocet-mexyl) is a safener that can be applied in combination with pesticides to reduce phytotoxicity to crops including wheat, barley, triticale, rye, teff, oats, corn, sorghum, rice, sugar cane and pasture grasses. When applied in combination with a pesticide, cloquintocet-mexyl can act as an antidote or antagonist to the effects of the pesticide on the crop and can reduce or prevent damage to the crop.

The safener complexes described herein can be formed from cloquintocet acid, or a salt thereof. In some embodiments, the safener complexes are substantially free of agriculturally acceptable esters of cloquintocet acid, such as cloquintocet-mexyl. In some embodiments, the safener complexes are used in combination with herbicides to reduce phytotoxicity to crops when the combination is used to control undesirable vegetation in the crops.

The safener complexes also contain an amine-containing polymer or oligomer. The molecular weight of the amine-containing polymer or oligomer can vary. In some embodiments, the amine-containing polymer or oligomer can have an average molecular weight of at least 250 Daltons (e.g., at least 300 Daltons, at least 350 Daltons, at least 400 Daltons, at least 450 Daltons, at least 500 Daltons, at least 550 Daltons, at least 600 Daltons, at least 650 Daltons, at least 700 Daltons, at least 750 Daltons, at least 800 Daltons, at least 850 Daltons, at least 900 Daltons, at least 950 Daltons, at least 1,000 Daltons, at least 1,050 Daltons, at least 1,100 Daltons, at least 1,150 Daltons, at least 1,200 Daltons, at least 1,250 Daltons, at least 1,500 Daltons, at least 1,750 Daltons, at least 2,000 Daltons, at least 2,500 Daltons, at least 5,000 Daltons, at least 10,000 Daltons, at least 50,000 Daltons, at least 100,000 Daltons, at least 500,000 Daltons, or at least 1,000,000 Daltons). In some embodiments, the amine-containing polymer or oligomer can have an average molecular weight of 2,000,000 Daltons or less (e.g., 1,000,000 Daltons or less, 500,000 Daltons or less, 300,000 Daltons or less, 100,000 Daltons or less, 50,000 Daltons or less, 30,000 Daltons or less, 10,000 Daltons or less, 5,000 Daltons or less, 2,500 Daltons or less, 2,000 Daltons or less, 1,750 Daltons or less, 1,500 Daltons or less, 1,250 Daltons or less, 1,200 Daltons or less, 1,150 Daltons or less, 1,100 Daltons or less, 1,050 Daltons or less, 1,000 Daltons or less, 950 Daltons or less, 900 Daltons or less, 850 Daltons or less, 800 Daltons or less, 750 Daltons or less, 700 Daltons or less, 650 Daltons or less, 600 Daltons or less, 550 Daltons or less, 500 Daltons or less, 450 Daltons or less, 400 Daltons or less, 350 Daltons or less, or 300 Daltons or less). The amine-containing polymer or oligomer can have an average molecular weight ranging from any of the minimum values described above to any of the maximum values described above. For example, the amine-containing polymer or oligomer can have an average molecular weight of from 250 to 2,000,000 Daltons (e.g., 300 to 1,000,000 Daltons, 350 to 500,000 Daltons, 400 to 100,000 Daltons, 450 to 50,000 Daltons, or 500 to 10,000 Daltons). In some embodiments, the amine-containing polymer or oligomer can have an average molecular weight of from 500 to 1,000,000 Daltons (e.g., from 550 to 1,000,000 Daltons, from 600 to 1,000,000 Daltons, from 650 to 1,000,000 Daltons, from 700 to 1,000,000 Daltons, from 750 to 1,000,000 Daltons, from 800 to 1,000,000 Daltons, from 850 to 1,000,000 Daltons, from 900 to 1,000,000 Daltons, from 950 to 1,000,000 Daltons, from 1,000 to 1,000,000 Daltons, from 1,050 to 1,000,000 Daltons, from 1,100 to 1,000,000 Daltons, from 1,150 to 1,000,000 Daltons, or from 1,200 to 1,000,000 Daltons). In certain embodiments, the amine-containing polymer or oligomer can have an average molecular weight of from 500 to 10,000 Daltons (e.g., from 550 to 10,000 Daltons, from 600 to 10,000 Daltons, from 650 to 10,000 Daltons, from 700 to 10,000 Daltons, from 750 to 10,000 Daltons, from 800 to 10,000 Daltons, from 850 to 10,000 Daltons, from 900 to 10,000 Daltons, from 950 to 10,000 Daltons, from 1,000 to 10,000 Daltons, from 1,050 to 10,000 Daltons, from 1,100 to 10,000 Daltons, from 1,150 to 10,000 Daltons, or from 1,200 to 10,000 Daltons).

In some cases, the amine-containing polymer or oligomer can have a nitrogen content of from 10 to 50 percent by weight, based on the total weight of the amine-containing polymer or oligomer (e.g., 15 to 45 percent or 20 to 40 percent). The amine-containing polymer or oligomer can contain independently of primary, secondary, and/or tertiary amine groups that can, as valency and stability permit, contain one or more alkyl or arylalkyl groups.

Examples of suitable amine-containing polymers and oligomers include, but are not limited to, polyamines, polymeric polyamines, nitrogen-substituted vinyl polymers, polyoxazolines, polypropyleneimine dendrimers, polyethyleneimine dendrimers, polyamidoamine dendrimers, combinations thereof, co-polymers thereof, and derivatives thereof. Examples of polyamines and polymeric polyamines include polyalkyleneimines, such as polyethyleneimines and polypropyleneimines, polyvinylamines, polyalkoxylated polyamines (e.g., ethoxylated polyamines and propoxylated polyamines), alkylated or benzylated polyamines, and combinations thereof. In some embodiments, the amine-containing polymer or oligomer can include a polyethyleneimine, a polyethyleneimine dendrimer, a blend thereof, a co-polymer thereof, or a derivative thereof. In some embodiments, the amine-containing polymer or oligomer can include a polyethyleneimine (PEI). Derivatives of the polymers and oligomers described above include polymers and oligomers that possess the polymer or oligomer backbones described above, but which include one or more additional moieties attached to the polymer or oligomer backbone (e.g., polymers or oligomers containing varying sidechains, or polymers or oligomers containing covalently modified amine groups, such as alkylated and/or alkoxylated amine groups).

Examples of suitable polyethyleneimines include linear and branched-chain polyethyleneimine polymers or oligomers including, for example, 10 or more monomer units, as well as derivatives, analogs, co-polymers, and mixtures thereof. Suitable polyethyleneimines can be prepared, for example, by the polymerization of ethyleneimine. Examples of commercially available polyethyleneimines include the LUPASOL® or EPOMIN® families of products such as, for example, LUPASOL® G20, LUPASOL®FG, LUPASOL® G35, LUPASOL® P, and LUPASOL® 1595 (the LUPASOL® series of products are commercially available from BASF, Florham Park, N.J.), and EPOMIN® SP-003, EPOMIN® SP-006, EPOMIN® SP-012, EPOMIN® SP-018, EPOMIN® SP-200, EPOMIN® SP-1000, and EPOMIN®

SP-1050 (the EPOMIN® series of products are commercially available from Nippon Shokubai, Osaka, Japan).

In some embodiments, the polyethyleneimine can include a branched, spherical polyamine with a well-defined ratio of primary, secondary, and/or tertiary amine functional groups.

In some embodiments, the polyethyleneimine can have a molar ratio of primary amines:secondary amines of at least 1:1.25 (e.g., at least 1:1.2, at least 1:1.15, at least 1:1.1, at least 1:1.05, at least 1:1, at least 1:0.95, at least 1:0.9, at least 1:0.85, or at least 1:0.8). In some embodiments, the polyethyleneimine can have a molar ratio of primary amines:secondary amines of 1:0.75 or less (e.g., 1:0.8 or less, 1:0.85 or less, 1:0.9 or less, 1:0.95 or less, 1:1 or less, 1:1.05 or less, 1:1.1 or less, 1:1.15, or 1:1.2 or less).

The polyethyleneimine can have a molar ratio of primary amines:secondary amines that ranges from any of the minimum values above to any of the maximum values above. For example, the polyethyleneimine can have a molar ratio of primary amines:secondary amines of from 1:1.25 to 1:0.75 (e.g., from 1:1.2 to 1:0.8, from 1:1.15 to 1:0.85, from 1:1.1 to 1:0.9, or from 1:1.05 to 1:0.95).

In some embodiments, the polyethyleneimine can have a molar ratio of primary amines:tertiary amines of at least 1:0.9 (e.g., at least 1:0.75, at least 1:0.6, at least 1:0.5, or at least 1:0.4). In some embodiments, the polyethyleneimine can have a molar ratio of primary amines:tertiary amines of 1:0.4 or less (e.g., 1:0.5 or less, 1:0.6 or less, 1:0.7 or less, 1:0.8 or less, or 1:0.9 or less).

The polyethyleneimine can have a molar ratio of primary amines:tertiary amines that ranges from any of the minimum values above to any of the maximum values above. For example, in some embodiments, the polyethyleneimine can have a molar ratio of primary amines:tertiary amines of from 1:0.90 to 1:0.40 (e.g., from 1:0.80 to 1:0.50, from 1:0.70 to 1:0.60, from 1:0.60 to 1:0.70, from 1:0.50 to 1:0.80, or from 1:0.40 to 1:0.90.

In some embodiments, the polyethyleneimine can have a molar ratio of primary amines:secondary amines:tertiary amines of 1:0.82:0.53. In some embodiments, the polyethyleneimine can have a molar ratio of primary amines:secondary amines:tertiary amines of 1:0.91:0.64. In some embodiments, the polyethyleneimine can have a molar ratio of primary amines:secondary amines:tertiary amines of 1:0.94:0.67.

In certain embodiments, the polyethyleneimine can be defined by the general formula below

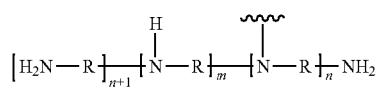

wherein R is an ethylene group (i.e., —CH$_2$CH$_2$—); [H$_2$N—R—] represents a primary amine moiety within the polyethyleneimine,

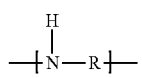

represents a secondary amine moiety within the polyethyleneimine,

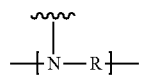

represents a tertiary amine moiety within the polyethyleneimine, and the value of n and m and the ratios thereof are selected so as to define a polyamine commercially available under the tradename LUPASOL®, such as LUPASOL® FG which is characterized by the following: an average molecular weight of approximately 800 g/mol; a viscosity of 800 mPa at 20° C.; a pour point of −3° C.; a density at 20° C. of 1.09 g/mL; and a ratio of primary:secondary:tertiary amine nitrogens of 1:0.82:0.53; LUPASOL® G20 water free which is characterized by the following: an average molecular weight of approximately 1,300 g/mol; a viscosity of 5,000 mPa at 20° C.; a pour point of −16° C.; a density at 20° C. of 1.03 g/mL; and a ratio of primary:secondary:tertiary amine nitrogens of 1:0.91:0.64; LUPASOL® PR 8515 which is characterized by the following: an average molecular weight of approximately 2,000 g/mol; a viscosity of from 300 mPa at 80° C. to 75,000 mPa at 20° C.; a pour point of −9° C.; a density at 20° C. of 1.05 g/mL; and a ratio of primary:secondary:tertiary amine nitrogens of 1:0.92:0.70; LUPASOL® WF which is characterized by the following: an average molecular weight of approximately 25,000 g/mol; a viscosity of from 2500 mPa at 80° C. to 200,000 mPa at 20° C.; a pour point of −3° C.; a density at 20° C. of 1.10 g/mL; and a ratio of primary:secondary:tertiary amine nitrogens of 1:1.2:0.76; LUPASOL® FC which is characterized by the following: an average molecular weight of approximately 800 g/mol; a viscosity of 250 mPa at 20° C.; a pour point of −24° C.; a density at 20° C. of 1.08 g/mL; and a ratio of primary:secondary:tertiary amine nitrogens of 1:0.86:0.42; LUPASOL® G20 (50% in water) which is characterized by the following: an average molecular weight of approximately 1,300 g/mol; a viscosity of 350 mPa at 20° C.; a pour point of −24° C.; a density at 20° C. of 1.08 g/mL; and a ratio of primary:secondary:tertiary amine nitrogens of 1:0.9:0.64; LUPASOL® G35 which is characterized by the following: an average molecular weight of approximately 2,000 g/mol; a viscosity of 450 mPa at 20° C.; a pour point of −18° C.; a density at 20° C. of 1.08 g/mL; and a ratio of primary:secondary:tertiary amine nitrogens of 1:0.94:0.67; LUPASOL® G100 which is characterized by the following: an average molecular weight of approximately 5,000 g/mol; a viscosity of 1200 mPa at 20° C.; a pour point of −18° C.; a density at 20° C. of 1.08 g/mL; and a ratio of primary:secondary:tertiary amine nitrogens of 1:1.05:0.76; LUPASOL® HF which is characterized by the following: an average molecular weight of approximately 25,000 g/mol; a viscosity of 14,000 mPa at 20° C.; a pour point of −20° C.; a density at 20° C. of 1.08 g/mL; and a ratio of primary:secondary:tertiary amine nitrogens of 1:1.2:0.76; LUPASOL® P which is characterized by the following: an average molecular weight of approximately 750,000 g/mol; a viscosity of from 1,000 mPa at 80° C. to 500,000 mPa at 20° C.; a pour point of −3° C., a density at 20° C. of 1.09 g/mL; and a ratio of primary:secondary:tertiary amine nitrogens of 1:1.07:0.77; LUPASOL® PS which is characterized by the following: an average molecular weight of approximately 750,000 g/mol; a viscosity of 1,400 mPa at 20° C.; a pour point of −5° C.; and a ratio of primary:secondary:tertiary amine nitrogens of 1:1.07:0.77; LUPASOL® SK which is characterized by the following: an average molecular weight of approximately 2,000,000 g/mol; a viscosity of 750 mPa at 20° C.; a pour point of 0° C.; and a density at 20° C. of 1.06 g/mL; LUPASOL® SNA which is characterized by the following: an average molecular weight of approximately 1,000,000 g/mol; a viscosity of 500 mPa at 20° C.; a pour point of 0° C.; and a density at 20° C. of 1.06 g/mL.

Examples of suitable polyvinylamines include linear polymers and copolymers derived from vinyl formamide monomers, and can include cationic and anionic polyvinylamine copolymers and charged or protonated polyvinylamines. These linear polyvinylamines are can be described by the following partial structural formula:

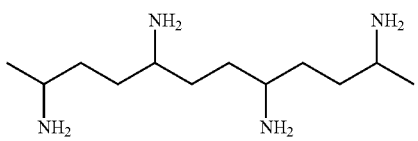 [SMILES: CC(N)CCC(N)CCC(N)CCC(C)N]

Examples of commercially available linear polyvinylamines include the LUPAMIN® family of products such as LUPAMIN® 1595, LUPAMIN® 4500, LUPAMIN® 5095, LUPAMIN® 9030, LUPAMIN® 9050, and LUPAMIN® 9095. Examples of commercially available cationic and anionic polyvinylamine copolymers include the LUREDUR® family of products, such as LUREDUR® AM na, LUREDUR® AV, LUREDUR® VH, LUREDUR® VI, LUREDUR® VM, LUREDUR® PR8094, LUREDUR® PR8261, and LUREDUR® PR8349. Examples of commercially available charged or protonated polyvinylamines include the CATIOFAST® family of products such as CATIOFAST® GM, CATIOFAST® PL, CATIOFAST® PR8236, CATIOFAST® VCB, CATIOFAST® VFH, CATIOFAST® VLW, CATIOFAST® VMP, and CATIOFAST® VSH. The LUPAMIN®, LUREDUR®, and CATIOFAST® series of products are commercially available from BASF (Florham Park, N.J.).

The relative amounts of the amine-containing polymer or oligomer and the cloquintocet acid, or salt thereof, in the safener complexes described herein can be described in terms of the weight ratio of cloquintocet acid, or salt thereof, on an AE basis to the amine-containing polymer or oligomer present in the safener complex.

In some embodiments, the weight ratio of cloquintocet acid, or salt thereof, on an AE basis to the amine-containing polymer or oligomer in the safener complex can be at least 1:2 (e.g., at least 1:1.5, at least 1:1, at least 1.5:1, at least 2:1, at least 3:1, at least 4:1, at least 5:1, at least 6:1, at least 7:1, at least 8:1 or at least 9:1). In some embodiments, the weight ratio of cloquintocet acid, or salt thereof, on an AE basis to the amine-containing polymer or oligomer in the safener complex can be 10:1 or less (e.g., 9:1 or less, 8:1 or less, 7:1 or less, 6:1 or less, 5:1 or less, 4:1 or less, 3:1 or less, 2:1 or less, 1.5:1 or less, 1:1 or less, or 1:1.5 or less). The weight ratio of cloquintocet acid, or salt thereof, on an AE basis to the amine-containing polymer or oligomer in the safener complex can range from any of the minimum values described above to any of the maximum values described above. For example, the weight ratio of cloquintocet acid, or a salt thereof, on an AE basis to the amine-containing polymer or oligomer can range from 1:2 to 10:1 (e.g., 1:1 to 9:1, 1:1 to 7:1, 2:1 to 5:1, or 2:1 to 4:1).

Safener complexes comprising cloquintocet acid, or a salt thereof, and an amine-containing polymer or oligomer can be formed by combining cloquintocet (e.g., the free acid form of cloquintocet, or a salt thereof,) and an amine-containing polymer or oligomer under conditions effective to form the safener complex. For example, cloquintocet acid, or a salt thereof, can be contacted with the amine-containing polymer or oligomer in a suitable solvent. Suitable solvents are generally polar in nature, and can include, but are not limited to, alcohols such as methanol, ethanol, ethylene glycol, and propylene glycol; derivatives of ethylene and propylene glycol such as alkylated ethylene glycols and oligomers thereof such as DOWANOL® EB, DB, TBH, DM, and TMH (the DOWANOL® series of products are available from The Dow Chemical Company (Midland, Mich.)), and propylene glycol butyl ether; ketones such as acetone, acetophenone, cyclohexanone, methyl ethyl ketone, and methyl iso-butyl ketone; sulfoxides or sulfones such as dimethyl sulfoxide and sulfolane; ethers such as tetrahydrofuran and dioxane; nitriles such as acetonitrile and butyronitrile; N,N-dialkyl amides such as, N-methyl-2-pyrrolidinone and N,N-dimethyl alkylamides; esters such as butyl lactate, and mixtures thereof, and mixtures of any of the above solvents with water.

If desired, the cloquintocet acid, or a salt thereof, and the amine-containing polymer or oligomer can be heated together to form the safener complex. In some embodiments, cloquintocet acid, or a salt thereof, can be contacted with the amine-containing polymer or oligomer at a temperature of at least 10° C. (e.g. at least 15° C., at least 20° C., at least 25° C., at least 30° C., at least 35° C., at least 40° C., at least 45° C., at least 50° C., at least 55° C., at least 60° C., at least 65° C., or at least 70° C.). In some embodiments, cloquintocet acid, or a salt thereof, can be contacted with the amine-containing polymer or oligomer at a temperature of 75° C. or less (e.g., 70° C. or less, 65° C. or less, 60° C. or less, 55° C. or less, 50° C. or less, 45° C. or less, 40° C. or less, 35° C. or less, 30° C. or less, 25° C. or less, 20° C. or less, or 15° C. or less). Cloquintocet acid, or a salt thereof, can be contacted with the amine-containing polymer or oligomer at a temperature ranging from any of the minimum values described above to any of the maximum values described above. For example, the safener complex can be formed by contacting cloquintocet acid, or a salt thereof, with an amine-containing polymer or oligomer at a temperature of from 10° C. to 75° C. (e.g., from 15° C. to 70° C., from 20° C. to 65° C., from 25° C. to 60° C., from 30° C. to 55° C., from 35° C. to 50° C., or from 40° C. to 45° C.).

Also provided are compositions that comprise the safener complex and a pesticide. The compositions can be, for example, an emulsifiable concentrate (EC), an oil-in-water emulsion concentrate (EW), a suspension emulsion concentrate (SE), a suspension concentrate (SC), a solid composition such as a granule or powder, or an aqueous spray solution or mixture. Such compositions can be prepared by combining a pesticide and a safener complex comprising cloquintocet acid, or a salt thereof, and an amine-containing polymer or oligomer, and any necessary or optional inert ingredients, using a variety of suitable methods known in the art.

The pesticide can be, for example, a fungicide, an insecticide, a herbicide, or a combination thereof. In certain embodiments, the pesticide can comprise a herbicide. The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "crops"

and "vegetation" can include, for instance, germinant seeds, emerging seedlings, and established vegetation.

In some embodiments, the pesticide can include an acetolactate synthase (ALS) inhibitor, an acetyl CoA carboxylase (ACCase) inhibitor, or a combination thereof. Examples of suitable pesticides include, for example, clodinafop-propargyl, flupyrsulfuron, pyroxsulam, and 4-aminopicolinic acid based herbicides. Examples of 4-aminopicolinic acid based herbicides, including halauxifen and halauxifen-methyl, are described in U.S. Pat. Nos. 7,314,849 and 7,432,227 to Balko et al., which are hereby incorporated by reference in their entireties. In certain embodiments, the composition can comprise pyroxsulam. Additional exemplary pesticides suitable for use in the compositions described herein include 2,4-D, acetochlor, aclonifen, amicarbazone, ametryn, amidosulfuron, aminopyralid, aminocyclopyrachlor, aminotriazole, ammonium thiocyanate, asulam, anilofos, atrazine, beflubutamid, benazolin, bentazone, bifenox, bromacil, bromoxynil, butachlor, butafenacil, butralin, butroxydim, carbetamide, carfentrazone, carfentrazone-ethyl, chlormequat, chlorsulfuron, chlortoluron, cinidon-ethyl, clethodim, clomazone, cyanazine, cyclosulfamuron, cycloxydim, dicamba, dichlobenil, dichlorprop, dichlorprop-P, diclofop-methyl, diclosulam, diflufenican, diflufenzopyr, dimefuron, dimethachlor, diquat, diuron, EPTC, ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, fluroxypyr, fluroxypyr-meptyl, flurtamone, gibberellic acid, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop, mecoprop-P, mesosulfuron, mesosulfuron-ethyl sodium, metazochlor, metosulam, metribuzin, metsulfuron, metsulfuron-methyl, MSMA, 1-napthaleneacetic acid, napropamide, nopropamide-M, norfurazon, orthosulfamuron, oryzalin, oxadiargyl, oxadiazon, oxyfluorfen, paraquat, pendimethalin, penoxsulam, picloram, picolinafen, pinoxaden, piperophos, primisulfuron, profluazol, prometon, propanil, propaquizafop, propoxycarbazone, propyzamide, prosulfocarb, prosulfuron, pyraflufen-ethyl (ET-751), pyrasulfotole, pyribenzoxim (LGC-40863), pyroxsulfone, quinclorac, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxidim, terbacil, terbutryn, thiazopyr, thiencarbazone-methyl, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof. In certain embodiments, the pesticide can include pyroxsulam, clodinafop-propargyl, pinoxaden, flupyrsulfuron, halauxifen, halauxifen-methyl, an agriculturally acceptable salt or ester thereof, or a combination thereof.

In compositions including a pesticide in combination with the safener complex, the weight ratio of (a) the pesticide to (b) the safener complex can be varied. In some embodiments, the weight ratio of (a) to (b) can be from 50:1 to 1:50, from 40:1 to 1:40, from 30:1 to 1:30, from 20:1 to 1:20, from 10:1 to 1:10, or from 5:1 to 1:5. In some embodiments, the weight ratio of (a) to (b) can be 1:1 or less (e.g., 1:1.5 or less, 1:2 or less, 1:2.5 or less, 1:3 or less, 1:4 or less, 1:5 or less, 1:6 or less, 1:7 or less, 1:8 or less, 1:9 or less, 1:10 or less, 1:15 or less, 1:20 or less, 1:30 or less, or 1:40 or less). In some embodiments, the weight ratio of (a) to (b) can be at least 1:45 (e.g., at least 1:40, at least 1:35, at least 1:30, at least 1:25, at least 1:20, at least 1:15, at least 1:10, at least 1:9, at least 1:8, at least 1:7, at least 1:6, at least 1:5, at least 1:4, at least 1:3, at least 1:2, at least 1:1.5, or at least 1:1) In some embodiments, the weight ratio of (a) to (b) can be at least 1:1 (e.g., at least 1.5:1, at least 2:1, at least 2.5:1, at least 3:1, at least 4:1, at least 5:1, at least 10:1, at least 15:1, at least 20:1, at least 25:1, at least 30:1, at least 35:1, at least 40:1, or at least 45:1). In some embodiments, the weight ratio of (a) to (b) can be 50:1 or less (e.g., 45:1 or less, 40:1 or less, 35:1 or less, 30:1 or less, 25:1 or less, 20:1 or less, 15:1 or less, 10:1 or less, 5:1 or less, 4:1 or less, 3:1 or less, 2.5:1 or less, 2:1 or less, or 1.5:1 or less). In compositions including a pesticide in combination with the safener complex, the weight ratio of (a) the pesticide to (b) the safener complex can range from any of the minimum values described above to any of the maximum values described above. For example, the weight ratio of (a) the pesticide to (b) the safener complex can be from 1:1 to 50:1 or from 1:1 to 1:50 (e.g., from 2.5:1 to 40:1, from 2.5:1 to 30:1, from 2.5:1 to 5:1, from 10:1 to 30:1, from 1:1 to 1:5, from 1:1 to 1:10, from 1:1 to 1:15, from 1:1 to 1:20, or from 1:1 to 1:30).

Optionally, the compositions provided herein can further include one or more additives. In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof.

Exemplary agriculturally acceptable adjuvants include, but are not limited to, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphate alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); and PEG (400) dioleate-99.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamin B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof.

The additive can also include a solid filler. Exemplary solid fillers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

The compositions disclosed herein can be applied in any known technique for applying pesticides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (i.e., before the emergence of undesirable vegetation) or post-emergence (i.e., during and/or after emergence of the undesirable vegetation). In some embodiments, the compositions disclosed herein are applied post-emergence when the undesirable vegetation starts with leaf development up to flowering. In some embodiments, the compositions disclosed herein are applied post-emergence to relatively immature undesirable vegetation to achieve the maximum control of weeds. In some embodiments when the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent to the vegetation or applying to soil or water to prevent the emergence or growth of vegetation by spraying (e.g., foliar spraying). In some embodiments, the spraying techniques use, for example, water as carrier and spray liquor rates of from 2 liters per hectare (L/ha) to 2000 L/ha (e.g., from 10-1000 L/ha, or from 50-500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that the spray comes into little contact, if any, with the leaves of the sensitive crop plants while reaching the leaves of undesirable vegetation that grows underneath or on the bare soil (e.g., post-directed or lay-by). In some embodiments, the compositions disclosed herein can be applied as dry formulations (e.g., granules, WDG's, etc.) into water.

In some embodiments, wherein the undesirable vegetation is treated post-emergence, the compositions disclosed herein are applied by foliar application. In some embodiments, herbicidal activity is exhibited by the composition when applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific active ingredient employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, wheat, barley, triticale, rye, teff, oats, corn, sorghum, rice, sugar cane and pasture grasses. In some embodiments, the crops are cereal crops. In some embodiments, the cereal crops are spring wheat and/or durum wheat.

The compositions and methods disclosed herein can also be used in crop plants that are resistant to, for instance, herbicides, pathogens, and/or insects. For example, the compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, synthetic auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenylpyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil.

The compositions and methods may be used in controlling undesirable vegetation in crops possessing multiple or stacked traits conferring tolerance to multiple chemistries and/or inhibitors of multiple modes of action. In some embodiments, the compositions described herein are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions provided herein can be effective against a variety of types of undesirable vegetation, including undesirable vegetation that frequently poses a challenge in crops by competing for water, sunlight and nutrients. In some embodiments, the compositions disclosed herein can be used for controlling undesirable vegetation including grasses, broadleaf weeds, sedge weeds, and combinations thereof.

In some embodiments, the compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis species* (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf) Cory/Rydb. Ex Hill (hemp sesbania, SEBEX), or *Sphenoclea zeylanica* Gaertn. (gooseweed, SPDZE).

In some embodiments, the compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compositions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago species* (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

The compositions and methods provided herein can be used to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action or via multiple resistance mechanisms.

By way of non-limiting illustration, examples of certain embodiments of the present disclosure are given below. Parts and percentages are on a per weight basis unless otherwise indicated.

EXAMPLES

Preparation of Concentrates Containing CQC:PEI Complexes

Preparation of 3:1 (w/w) CQC:PEI Complexes in Ethylene Glycol N-Butyl Ether

Method 1

Three cloquintocet acid-polyethyleneimine (CQC:PEI) complexes were prepared as follows using the reagents described in Table 1. A polyethyleneimine (PEI) was added to DOWANOL EB (ethylene glycol n-butyl ether), and the resulting mixture was stirred to form a colorless solution. Solid cloquintocet acid (CQC) was added at a 3:1 weight ratio of CQC:PEI. To accelerate the reaction, the mixture was warmed up to 45° C. The white solids of CQC dissolved under constant stirring to form a dark yellow/orange solution, indicating the formation of a cloquintocet acid-polyethyleneimine (CQC:PEI) complex.

The resulting concentrates containing the CQC-PEI complexes were not soluble in water. Sample 1 separated from the water phase 30 minutes after dilution in water at 5%, 10% and 20% by weight relative to water.

TABLE 1

Preparation of 3:1 (w/w) CQC-PEI Complexes in Ethylene Glycol N-Butyl Ether.

| Component | Assay | Sample 1 | Sample 2 | Sample 3 |
|---|---|---|---|---|
| CQC (cloquintocet acid) | 99.4% | 15.09 g | 15.09 g | 6.04 g |
| LUPASOL FG (PEI) | 98% | 5.10 g | — | — |
| LUPASOL G20 water free (PEI) | 98% | — | 5.10 g | — |
| LUPASOL G35 (PEI) | 50% | — | — | 4.00 g |
| DOWANOL EB (solvent) | — | 29.81 g | 29.81 g | 19.96 g |
| Total Weight | | 50.00 g | 50.00 g | 30.00 g |

Method 2

Solid CQC was added to DOWANOL EB to form a slurry. A PEI was added to the slurry. Upon constant stirring at room temperature, the CQC gradually reacted with the PEI to form an orange solution of the CQC-PEI complex.

Preparation of a 3:1 (w/w) CQC:PEI Complex in a Mixture of Cyclohexanone and Ethylene Glycol N-Butyl Ether PEI (LUPASOL FG) was added to a 1:1 (w/w) mixture of cyclohexanone and DOWANOL EB (ethylene glycol n-butyl ether) using the amounts shown in Table 2. The mixture formed a clear solution upon stirring. Solid CQC was added to the solution. The CQC gradually dissolved to form an amber solution of the CQC-PEI complex.

TABLE 2

Preparation of a 3:1 CQC:PEI Complex in Cyclohexanone and Ethylene Glycol N-Butyl Ether

| Component | purity | Wt % | Sample 4 |
|---|---|---|---|
| CQC (cloquintocet acid) | 99% | 20 | 6.04 g |
| LUPASOL FG (PEI) | 98% | 6.67 | 2.04 g |
| DOWANOL EB (ethylene glycol n-butyl ether) | — | — | 10.96 g |
| Cyclohexanone | — | — | 10.96 g |
| Total Weight | | | 30.00 g |

Preparation of a 3:1 CQC:PEI Complex in 2-Propoxyethanol

PEI (LUPASOL G20) was dissolved in 2-propoxyethanol using the amounts shown in Table 3 to form a transparent solution. CQC was added to the solution. The CQC gradually dissolved upon constant stirring to form an orange solution.

TABLE 3

Preparation of a 3:1 CQC:PEI Complex in 2-Propoxyethanol

| Component | Assay | Wt % | Sample 5 |
|---|---|---|---|
| CQC (cloquintocet acid) | 99.4% | 30 | 15.09 g |
| LUPASOL G20 water free (PEI) | 98% | 10 | 5.10 g |
| 2-propoxyethanol | — | — | 29.81 g |
| Total Weight | | | 50.00 g |

Preparation of a 2.5:1 CQC:PEI Complex in 2-Propoxyethanol

PEI (LUPASOL G35) was dissolved in 2-propoxyethanol using the amounts shown in Table 4 to form a milky solution. CQC was added to the solution. The CQC gradually dissolved upon constant stirring to form a brownish-yellow solution.

TABLE 4

Preparation of a 2.5:1 CQC:PEI Complex in 2-Propoxyethanol

| Component | Assay | Wt % | Sample 6 |
|---|---|---|---|
| CQC (cloquintocet acid) | 99.4% | 20 | 6.04 g |
| LUPASOL G35 (PEI) | 50% | 8 | 4.8 g |
| 2-propoxyethanol | — | 63.88 | 19.16 g |
| water (from LUPASOL G35) | — | 8 | |
| Total Weight | | | 30.00 g |

Preparation of 2:1 CQC:PEI complexes in Ethylene Glycol N-Butyl Ether

Three cloquintocet acid-polyethyleneimine (CQC:PEI) complexes were prepared as follows using the reagents shown in Table 5. A PEI was added to DOWANOL EB (ethylene glycol n-butyl ether), and the resulting mixture was stirred to form a colorless solution. Solid cloquintocet acid (CQC) was added at a 2:1 weight ratio of CQC:PEI. To accelerate the reaction, the mixture was warmed up to 45° C. The white solids of CQC dissolved under constant stirring to form a dark yellow/orange solution, indicating the formation of a cloquintocet acid-polyethyleneimine (CQC:PEI) complex.

TABLE 5

Preparation of 2:1 CQC:PEI Complexes in Ethylene Glycol N-Butyl Ether

| Component | Assay | Sample 7 | Sample 8 | Sample 9 |
|---|---|---|---|---|
| CQC (cloquintocet acid) | 99.4% | 9.05 g | 6.04 g | 6.04 g |
| LUPASOL FG (PEI) | 98% | 4.59 g | — | — |
| LUPASOL G20 water free (PEI) | 98% | — | 3.06 g | — |
| LUPASOL G35 (PEI) | 50% | — | — | 3.00 g |
| DOWANOL EB (ethylene glycol n-butyl ether) | — | 16.35 g | 20.90 g | 17.96 g |
| water (from LUPASOL G35) | — | — | — | 3.00 g |
| Total Weight | | 30.00 g | 30.00 g | 30.00 g |

Preparation of a 1:1 CQC:PEI Complex in Ethylene Glycol N-Butyl Ether

A 1:1 CQC:PEI complex in ethylene glycol n-butyl ether was prepared using Method 1 and the reagents shown in Table 6.

TABLE 6

Preparation of 1:1 CQC:PEI Complex in Ethylene Glycol N-Butyl Ether

| Component | Assay | Wt % | Sample 10 |
|---|---|---|---|
| CQC (cloquintocet acid) | 99.4% | 20 | 6.04 g |
| LUPASOL G20 water free (PEI) | 98% | 20 | 6.12 g |
| DOWANOL EB (ethylene glycol n-butyl ether) | — | — | 17.84 g |
| Total Weight | | | 30.00 g |

Preparation of Formulations Containing CQC-PEI Complexes

Preparation of Formulation Containing CQC-PEI Complex: Formulation 1

An aromatic fluid (AROMATIC 200 ND; commercially available from ExxonMobil Corp.), a nonionic high HLB surfactant (ATLAS™ G-5000, a polyalkylene oxide block copolymer surfactant commercially available from Croda International PLC), and a second nonionic low HLB surfactant (ATLOX™ 4914, a polymeric surfactant commercially available from Croda International PLC) were combined with a 1.73 g of Sample 2 (Table 1) using the amounts shown in Table 7. The mixture was warmed in a microwave oven to form a homogeneous dark orange solution (Formulation 1), which readily formed an emulsion upon dilution in water.

TABLE 7

Preparation of Formulation 1.

| Component | Weight (g) |
|---|---|
| CQC (cloquintocet acid) | 0.53 |
| LUPASOL G20 water free (PEI) | 0.17 |
| DOWANOL EB (ethylene glycol n-butyl ether) | 1.03 |
| AROMATIC 200 ND | 0.80 |
| ATLAS G-5000 | 0.30 |
| ATLOX 4914 | 0.15 |
| Total Weight | 2.98 |

Preparation of Formulation Containing CQC-PEI Complex: Formulation 2

A nonionic high HLB surfactant (ATLAS™ G-5000, a polyalkylene oxide block copolymer surfactant commercially available from Croda International PLC), and a second surfactant (MAKON® TD-3, an ethoxylated tridecyl alcohol surfactant commercially available from Croda International PLC) were combined with a 4.23 g of Sample 4 (Table 2) using the amounts shown in Table 8. The mixture was warmed in a microwave oven to form a homogeneous amber solution (Formulation 2), which readily formed an emulsion upon dilution in water.

TABLE 8

Preparation of Formulation 2.

| Component | Weight (g) |
|---|---|
| CQC (cloquintocet acid) | 0.85 |
| LUPASOL G20 water free (PEI) | 0.28 |
| DOWANOL EB (ethylene glycol n-butyl ether) | 1.55 |
| Cyclohexanone | 1.55 |
| ATLAS G-5000 | 0.50 |
| MAKON® TD-3 | 0.25 |
| Total Weight | 4.98 |

Preparation of Formulation Containing CQC-PEI Complex: Formulation 3

DOWANOL EB (ethylene glycol n-butyl ether), a nonionic high HLB surfactant (ATLAS™ G-5000, a polyalkylene oxide block copolymer surfactant commercially available from Croda International PLC), and a second surfactant (MAKON® TD-3, an ethoxylated tridecyl alcohol surfactant commercially available from Croda International PLC) were combined with a 2.83 g of Sample 7 (Table 5) using the amounts shown in Table 9. The mixture was warmed in microwave oven to form a homogeneous brownish-yellow solution (Formulation 3), which readily formed an emulsion upon dilution in water.

TABLE 9

Preparation of Formulation 3.

| Component | Weight (g) |
|---|---|
| CQC (cloquintocet acid) | 0.85 |
| LUPASOL FG (PEI) | 0.42 |
| DOWANOL EB (ethylene glycol n-butyl ether) | 2.96 |
| ATLAS G-5000 | 0.50 |
| MAKON® TD-3 | 0.25 |
| Total Weight | 4.98 |

Preparation of Formulation Containing CQC-PEI Complex: Formulation 4

DOWANOL EB (ethylene glycol n-butyl ether), a nonionic high HLB surfactant (ATLAS™ G-5000, a polyalkylene oxide block copolymer surfactant commercially available from Croda International PLC), and a second surfactant (MAKON® TD-3, an ethoxylated tridecyl alcohol surfactant commercially available from Croda International PLC) were combined with a 4.25 g of Sample 3 (Table 1) using the amounts shown in Table 10. The mixture was warmed in a microwave oven to form a homogeneous brownish-yellow solution (Formulation 4), which readily formed an emulsion upon dilution in water.

TABLE 10

Preparation of Formulation 4.

| Component | Weight (g) |
|---|---|
| CQC (cloquintocet acid) | 0.85 |
| LUPASOL G35 (PEI) | 0.28 |
| DOWANOL EB (ethylene glycol n-butyl ether) | 3.83 |
| ATLAS G-5000 | 0.50 |
| MAKON® TD-3 | 0.25 |
| water (from LUPASOL G35) | 0.28 |
| Total Weight | 5.99 |

Preparation of Sample CQC-PEI Complexes for Use in Greenhouse Trials

Preparation of Greenhouse Sample Complex 1: 3:1 (w/w) CQC:Lupasol FG

Using the ingredients and amounts shown in Table 11, CQC, Lupasol FG (PEI) and 2-propoxyethanol 7 g) were combined and stirred for a sufficient period of time to form the CQC:PEI complex as described herein. The solution of the CQC:PEI complex was then treated with the remaining ingredients and stirred at ambient temperature or with sufficient heating to provide the sample of Complex 1 as a colored solution.

TABLE 11

Preparation of Greenhouse Sample: Complex 1

| Component | Wt % | Weight (g) |
|---|---|---|
| CQC (cloquintocet acid) | 17.50 | 3.52 |
| Lupasol FG (PEI) | 5.83 | 1.19 |
| 2-propoxyethanol | 35.30 | 7.06 |
| Aromatic 200 | 19.50 | 3.90 |
| 2-propoxyethanol | 6.67 | 1.33 |
| Termul 203 | 10.00 | 2.00 |
| Makon TD-3 | 5.00 | 1.00 |
| Total | 98.8 | 20.00 |

Preparation of Greenhouse Sample Complex 2: 2.5:1 (w/w) CQC:Lupasol G20

To 14.20 g of Dowanol EB was added 0.80 g Lupasol G20 (water free) to form a colorless solution. Then, 2.00 g of solid CQC was added. Upon constant stirring, the white solid of CQC dissolved to form a dark yellow solution. To the solution were then added 2.00 g of Atlas G5000 and 1.00 g of Makon TD-3 and the resulting mixture was warmed in a microwave oven to form a homogeneous brownish-yellow solution, which readily formed an emulsion upon dilution in water.

TABLE 12

Preparation of Greenhouse Sample: Complex 2

| Component | Wt % | Weight (g) |
|---|---|---|
| CQC (cloquintocet acid) | 10.00 | 2.00 |
| Lupasol G20 (water free) (PEI) | 4.00 | 0.80 |
| Dowanol EB | 71.00 | 14.20 |
| Atlas G5000 | 10.00 | 2.00 |
| Makon TD-3 | 5.00 | 1.00 |
| Total | | 20.00 |

Preparation of Greenhouse Sample Complex 3: 2:1 (w/w) CQC:Lupasol G35

Using the ingredients and amounts shown in Table 13, CQC, Lupasol G35 (PEI) and Dowanol EB were combined and stirred for a sufficient period of time to form the CQC:PEI complex as described herein.

TABLE 13

Preparation of Greenhouse Sample Complex 3

| Component | Wt % | Weight (g) |
|---|---|---|
| CQC (cloquintocet acid) | 20.00 | 6.04 |
| Lupasol G35 (50% in water) (PEI) | 10.00 | 3.00 |
| Dowanol EB | 59.88 | 17.96 |
| water (from Lupasol G35) | 10.00 | 3.00 |
| Total | 99.88 | 30.00 |

Preparation of Greenhouse Sample Complex 4: 1:1 (w/w) CQC:Lupasol G35

Using the ingredients and amounts shown in Table 14, CQC, Lupasol G35 (PEI) and Dowanol EB were combined and stirred for a sufficient period of time to form the CQC:PEI complex as described herein.

TABLE 14

Preparation of Greenhouse Sample: Complex 4

| Component | Wt % | Weight (g) |
|---|---|---|
| CQC (cloquintocet acid) | 10.00 | 3.02 |
| Lupasol G35 (50% in water) (PEI) | 10.00 | 3.00 |
| Dowanol EB | 69.94 | 20.98 |
| water (from Lupasol G35) | 10.00 | 3.00 |
| Total | | 30.00 |

Greenhouse Trials Using Pyroxsulam Herbicide and CQC: PEI Safener Complexes

Plant material was propagated in the Indianapolis greenhouses under cool temperature conditions of 18° C. and a 16 hour day length and 8 hour dark cycle. Seeds of each species were planted in 10 cm square pots containing Metro-Mix potting soil. Plants were top watered prior to treatment and sub-irrigated after treatment. Appropriate amounts of pyroxsulam and cloquintocet safener samples were weighed and diluted with a pH 7 monobasic potassium phosphate buffer, sourced from Ricca Chemical Company. The pH 7 buffer was used to avoid a potential pyroxsulam solubility issue when pyroxsulam and CQC-acid are mixed. Together, pyroxsulam and CQC-acid can acidify the spray solution. As pH decreases the solubility of pyroxsulam also decreases which could potentially result in precipitation of pyroxsulam and inaccurate crop injury observations.

Pyroxsulam was combined (tank-mixed) with each CQC-PEI complex and applied to spring wheat (TRZAS) and durum wheat (TRZDU). The phytotoxicity of these herbicide—safener combinations was evaluated for percent visual injury. The crop plants were treated with post-emergence foliar applications when they reached 4-5 leaves, 1 tiller and 12-14 cm in height. In addition, the efficacy of these herbicide—safener combinations was evaluated on wild oats (AVEFA) and annual ryegrass (LOLMG) for percent visual weed control. Treatments were applied to weeds at the 2 to 3 leaf stage. All results were compared to standard pyroxsulam formulations containing cloquintocet-mexyl as a safener (Standard 1), cloquintocet acid as a safener (Standard 2), and containing no safener (Standard 3) as described in Table 15.

All treatments were applied to selected plant species with a track sprayer (Generation III Research Sprayer manufactured by DeVries Manufacturing in Hollandale, Minn., USA) located in building 306, laboratory E1-483, at the Dow AgroSciences facility in Indianapolis, Ind. The track sprayer was calibrated to deliver 50 L/ha at 40 psi (262 kPa) pressure utilizing an 8001 E even, flat fan nozzle. Track sprayer speed was set at 1.8 mph (2.9 km h$^{-1}$). Applications were made to replicates of each species in a non-randomized complete block trial design, with 3 replications per treatment.

The treated plants and control plants were rated blind at various intervals after application. Ratings were based on a scale of 0-100%, wherein 0% indicates no injury or control of the vegetation and 100% indicates complete death of the plants. The herbicide tank-mix combinations tested, application rates and ratios employed, plant species tested, and results are given below.

TABLE 15

Standard Pyroxsulam Formulations Evaluated in Greenhouse Trials.

| Component | Standard 1 | Standard 2 | Standard 3 |
|---|---|---|---|
| Pyroxsulam | 2.88% | 21.5% | 50% |
| Safener | Cloquintocet-Mexyl 8.65% | Cloquintocet Acid 45.15% | No Safener |

TABLE 16

CQC-PEI Complexes Evaluated in Greenhouse Trials.

| CQC-PEI Complex Samples | CQC:PEI (weight ratio) | PEI | PEI MW |
|---|---|---|---|
| Complex 1 | 3:1 | LUPASOL FG | 800 |
| Complex 2 | 2.5:1 | LUPASOL G20 | 1300 |
| Complex 3 | 2:1 | LUPASOL G35 | 2000 |
| Complex 4 | 1:1 | LUPASOL G35 | 2000 |

The crop tolerance trials were applied on spring wheat (TRZAS) and durum wheat (TRZDU) are described in Table 17. Pyroxsulam was applied at 9.4, 18.8, and 37.6 g ai/ha to test plants of spring wheat and durum wheat. All treatments contained a tank-mixed adjuvant (a nonionic wetting and spreading agent, nonylphenoxy polyethoxy ethanol) commercially available under the trade name AGRAL® 90 from Syngenta. The rate of AGRAL 90 was 0.25% v/v, equal to 0.15 mL adjuvant/60 mL mixture.

TABLE 17

Crop Tolerance Trial Applied on Spring Wheat and Durum Wheat: Tank-mix Treatment Descriptions

| Trial No. | Standard No. | Herbicide (Pyroxsulam) Form. Type | g ai/ kg or L | rate (g ai/ha) | Safener | Form. Type | % ae by wt | CQC rate (g ae/ha) |
|---|---|---|---|---|---|---|---|---|
| 1 | 1 | OD | 30 | 9.4 | CQ-M | Built-In | | 19.7 |
| 2 | 1 | OD | 30 | 18.8 | CQ-M | Built-In | | 39.5 |
| 3 | 1 | OD | 30 | 37.6 | CQ-M | Built-In | | 79 |
| 4 | 2 | WG | 215 | 9.4 | CQ-Acid | Built-In | | 19.7 |
| 5 | 2 | WG | 215 | 18.8 | CQ-Acid | Built-In | | 39.5 |
| 6 | 2 | WG | 215 | 37.6 | CQ-Acid | Built-In | | 79 |
| 7 | 3 | WG | 500 | 9.4 | | None | | |
| 8 | 3 | WG | 500 | 18.8 | | None | | |
| 9 | 3 | WG | 500 | 37.6 | | None | | |
| 10 | 3 | WG | 500 | 9.4 | Complex 1 | EC | 17.5 | 19.7 |
| 11 | 3 | WG | 500 | 18.8 | Complex 1 | EC | 17.5 | 39.5 |
| 12 | 3 | WG | 500 | 37.6 | Complex 1 | EC | 17.5 | 79 |
| 13 | 3 | WG | 500 | 9.4 | Complex 2 | EC | 10 | 19.7 |
| 14 | 3 | WG | 500 | 18.8 | Complex 2 | EC | 10 | 39.5 |
| 15 | 3 | WG | 500 | 37.6 | Complex 2 | EC | 10 | 79 |
| 16 | 3 | WG | 500 | 9.4 | Complex 3 | EC | 20 | 29 |
| 17 | 3 | WG | 500 | 18.8 | Complex 3 | EC | 20 | 58 |
| 18 | 3 | WG | 500 | 37.6 | Complex 3 | EC | 20 | 116 |
| 19 | 3 | WG | 500 | 9.4 | Complex 4 | EC | 10 | 19.7 |
| 20 | 3 | WG | 500 | 18.8 | Complex 4 | EC | 10 | 39.5 |
| 21 | 3 | WG | 500 | 37.6 | Complex 4 | EC | 10 | 79 |

Durum tolerance to pyroxsulam formulations was assessed at 7 days after application (DAA) (Table 18), and 14 DAA (Table 19). Durum tolerance to treatments including CQC-PEI complexes was good, and comparable to standards. At 14 DAA, the treatments of pyroxsulam applied in combination with CQC-PEI safener complexes were found to exhibit less phytotoxicity than pyroxsulam applied in combination with cloquintocet-mexyl and similar levels of phytotoxicity to pyroxsulam applied in combination with cloquintocet acid (see Table 19).

Spring wheat tolerance to pyroxsulam formulations was assessed at 7 DAA (Table 20), 14 DAA (Table 21), and 21 DAA (Table 22). Spring wheat tolerance to formulations including CQC-PEI complexes at 7 DAA and 14 DAA was good, and comparable to standards. At 21 DAA, the treatments of pyroxsulam applied in combination with Complex 4 were found to exhibit less phytotoxicity than pyroxsulam applied in combination with cloquintocet-mexyl and similar levels of phytotoxicity to pyroxsulam applied in combination with cloquintocet acid (Table 21). At 21 DAA, the treatments of pyroxsulam applied in combination with Complexes 1-3 were found to exhibit similar levels of phytotoxicity to pyroxsulam applied in combination with cloquintocet-mexyl (Table 22).

TABLE 18

Durum Wheat Injury with Pyroxsulam Alone and with Several Cloquintocet Safener Formulations 7 Days after Application.

| Pyroxsulam Rate (g ai/ha) | Standard 1 | Standard 2 | Standard 3 | Standard 3 + Complex 1 | Standard 3 + Complex 2 | Standard 3 + Complex 3 | Standard 3 + Complex 4 |
|---|---|---|---|---|---|---|---|
| | | | | % Injury | | | |
| 9.4 | 17 | 18 | 35 | 25 | 22 | 28 | 26 |
| 18.8 | 22 | 23 | 35 | 27 | 28 | 32 | 31 |
| 37.6 | 32 | 32 | 38 | 30 | 32 | 32 | 33 |

TABLE 19

Durum Wheat Injury with Pyroxsulam Alone and with Several Cloquintocet Safener Formulations 14 Days after Application.

| Pyroxsulam Rate (g ai/ha) | Standard 1 | Standard 2 | Standard 3 | Standard 3 + Complex 1 | Standard 3 + Complex 2 | Standard 3 + Complex 3 | Standard 3 + Complex 4 |
|---|---|---|---|---|---|---|---|
| | | | | % Injury | | | |
| 9.4 | 18 | 12 | 47 | 17 | 12 | 18 | 15 |
| 18.8 | 32 | 13 | 50 | 22 | 17 | 20 | 17 |
| 37.6 | 43 | 23 | 58 | 22 | 27 | 22 | 25 |

TABLE 20

Spring Wheat Injury with Pyroxsulam Alone and with Several
Cloquintocet Safener Formulations 7 Days after Application.

| Pyroxsulam Rate (g ai/ha) | Standard 1 | Standard 2 | Standard 3 | Standard 3 + Complex 1 | Standard 3 + Complex 2 | Standard 3 + Complex 3 | Standard 3 + Complex 4 |
|---|---|---|---|---|---|---|---|
| | | | | % Injury | | | |
| 9.4 | 22 | 23 | 27 | 18 | 19 | 17 | 18 |
| 18.8 | 29 | 23 | 20 | 27 | 25 | 22 | 22 |
| 37.6 | 32 | 32 | 32 | 30 | 30 | 25 | 27 |

TABLE 21

Spring Wheat Injury with Pyroxsulam Alone and with Several Cloquintocet
Safener Formulations 14 Days after Application.

| Pyroxsulam Rate (g ai/ha) | Standard 1 | Standard 2 | Standard 3 | Standard 3 + Complex 1 | Standard 3 + Complex 2 | Standard 3 + Complex 3 | Standard 3 + Complex 4 |
|---|---|---|---|---|---|---|---|
| | | | | % Injury | | | |
| 9.4 | 20 | 17 | 35 | 18 | 17 | 22 | 17 |
| 18.8 | 33 | 17 | 37 | 28 | 25 | 27 | 23 |
| 37.6 | 45 | 28 | 45 | 37 | 40 | 35 | 25 |

TABLE 22

Spring Wheat Injury with Pyroxsulam Alone and with Several Cloquintocet
Safener Formulations 21 Days after Application.

| Pyroxsulam Rate (g ai/ha) | Standard 1 | Standard 2 | Standard 3 | Standard 3 + Complex 1 | Standard 3 + Complex 2 | Standard 3 + Complex 3 | Standard 3 + Complex 4 |
|---|---|---|---|---|---|---|---|
| | | | | % Injury | | | |
| 9.4 | 12 | 2 | 57 | 12 | 13 | 12 | 7 |
| 18.8 | 18 | 7 | 65 | 12 | 12 | 17 | 10 |
| 37.6 | 42 | 10 | 78 | 22 | 22 | 28 | 12 |

The efficacy of treatments including pyroxsulam in combination with CQC-PEI complexes was evaluated in wild oats (AVEFA) and annual ryegrass (LOLMG) as described in Table 23. In this trial, pyroxsulam was applied at 1.2, 2.4, and 4.8 g ai/ha to the test pots. All formulations also contained an adjuvant (a nonionic wetting and spreading agent (nonylphenoxy polyethoxy ethanol) commercially available under the trade name AGRAL® 90 from Syngenta; adjuvant rate of 0.25% v/v, 0.15 mL adjuvant/60 mL mixture).

TABLE 23

Weed Control Trials Performed in Wild Oats and Annual
Ryegrass: Tank-mix Treatment Descriptions

| | Herbicide (Pyroxsulam) | | | | Safener | | | |
|---|---|---|---|---|---|---|---|---|
| Trial No. | Standard No. | Form. Type | g ai/ kg or L | rate (g ai/ha) | Safener | Form. Type | % ae by wt | CQC rate (g ae/ha) |
| 22 | 2 | WG | 215 | 1.2 | CQ-Acid Built-In | | | 2.5 |
| 23 | 2 | WG | 215 | 2.4 | CQ-Acid Built-In | | | 5 |
| 24 | 2 | WG | 215 | 4.8 | CQ-Acid Built-In | | | 10 |
| 25 | 3 | WG | 500 | 1.2 | None | | | |
| 26 | 3 | WG | 500 | 2.4 | None | | | |
| 27 | 3 | WG | 500 | 4.8 | None | | | |
| 28 | 3 | WG | 500 | 1.2 | Complex 1 | EC | 17.5 | 2.5 |
| 29 | 3 | WG | 500 | 2.4 | Complex 1 | EC | 17.5 | 5 |
| 30 | 3 | WG | 500 | 4.8 | Complex 1 | EC | 17.5 | 10 |
| 31 | 3 | WG | 500 | 1.2 | Complex 2 | EC | 10 | 2.5 |
| 32 | 3 | WG | 500 | 2.4 | Complex 2 | EC | 10 | 5 |
| 33 | 3 | WG | 500 | 4.8 | Complex 2 | EC | 10 | 10 |
| 34 | 3 | WG | 500 | 1.2 | Complex 3 | EC | 20 | 3.7 |
| 35 | 3 | WG | 500 | 2.4 | Complex 3 | EC | 20 | 7.4 |
| 36 | 3 | WG | 500 | 4.8 | Complex 3 | EC | 20 | 14.7 |

TABLE 23-continued

Weed Control Trials Performed in Wild Oats and Annual Ryegrass: Tank-mix Treatment Descriptions

| Trial No. | Standard No. | Herbicide (Pyroxsulam) Form. Type | g ai/ kg or L | rate (g ai/ha) | Safener | Form. Type | % ae by wt | CQC rate (g ae/ha) |
|---|---|---|---|---|---|---|---|---|
| 37 | 3 | WG | 500 | 1.2 | Complex 4 | EC | 10 | 2.5 |
| 38 | 3 | WG | 500 | 2.4 | Complex 4 | EC | 10 | 5 |
| 39 | 3 | WG | 500 | 4.8 | Complex 4 | EC | 10 | 10 |

The efficacy of the treatments described in Table 23 against wild oats was assessed at 14 DAA (Table 24) and 21 DAA (Table 25). Treatments of pyroxsulam applied in combination with CQC-PEI safener complexes exhibited similar weed control to pyroxsulam applied in combination with cloquintocet acid.

TABLE 24

Wild oat control with pyroxsulam alone and with several cloquintocet safener formulations 14 days after application.

| Pyroxsulam Rate (g ai/ha) | Standard 2 | Standard 3 | Standard 3 + Complex 1 | Standard 3 + Complex 2 | Standard 3 + Complex 3 | Standard 3 + Complex 4 |
|---|---|---|---|---|---|---|
| | | | % Control | | | |
| 1.2 | 75 | 95 | 87 | 82 | 87 | 72 |
| 2.4 | 97 | 97 | 95 | 92 | 96 | 88 |
| 4.8 | 98 | 99 | 99 | 97 | 98 | 99 |

TABLE 25

Wild oat control with pyroxsulam alone and with several cloquintocet safener formulations 21 days after application.

| Pyroxsulam Rate (g ai/ha) | Standard 2 | Standard 3 | Standard 3 + Complex 1 | Standard 3 + Complex 2 | Standard 3 + Complex 3 | Standard 3 + Complex 4 |
|---|---|---|---|---|---|---|
| | | | % Control | | | |
| 1.2 | 75 | 98 | 93 | 92 | 90 | 77 |
| 2.4 | 98 | 99 | 95 | 95 | 98 | 98 |
| 4.8 | 99 | 100 | 99 | 97 | 100 | 99 |

The efficacy of the treatments described in Table 23 against annual ryegrass was assessed at 14 DAA (Table 26) and 21 DAA (Table 27). As shown in Tables 26 and 27, the efficacy treatments of pyroxsulam applied in combination with CQC-PEI safener complexes against annual ryegrass was generally good. At lower rates, treatments of pyroxsulam applied in combination with Complexes 3 and 4 resulted in lower efficacy than Standards 2 and 3. Treatments of pyroxsulam applied in combination with Complexes 1 and 2 provided good control of annual ryegrass.

TABLE 26

Annual ryegrass control with pyroxsulam alone and with several cloquintocet safener formulations 14 days after application.

| Pyroxsulam Rate (g ai/ha) | Standard 2 | Standard 3 | Standard 3 + Complex 1 | Standard 3 + Complex 2 | Standard 3 + Complex 3 | Standard 3 + Complex 4 |
|---|---|---|---|---|---|---|
| | | | % Control | | | |
| 1.2 | 70 | 75 | 78 | 77 | 58 | 68 |
| 2.4 | 85 | 88 | 93 | 95 | 73 | 72 |
| 4.8 | 93 | 98 | 98 | 99 | 95 | 97 |

TABLE 27

Annual ryegrass control with pyroxsulam alone and with several cloquintocet safener formulations 21 days after application.

| Pyroxsulam Rate (g ai/ha) | Standard 2 | Standard 3 | Standard 3 + Complex 1 | Standard 3 + Complex 2 | Standard 3 + Complex 3 | Standard 3 + Complex 4 |
|---|---|---|---|---|---|---|
| | | | % Control | | | |
| 1.2 | 38 | 65 | 48 | 52 | 18 | 38 |
| 2.4 | 63 | 82 | 92 | 88 | 50 | 52 |
| 4.8 | 83 | 97 | 97 | 99 | 89 | 97 |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A composition comprising a safener complex and a pesticide, wherein:
   the safener complex comprises cloquintocet acid, or a salt thereof, and an amine-containing polymer or oligomer;
   the weight ratio of the cloquintocet acid, or salt thereof, to the amine-containing polymer or oligomer ranges from 1:2 to 10:1; and
   the amine-containing polymer or oligomer includes a branched, spherical polyethyleneimine.

2. The composition of claim 1, wherein the amine-containing polymer or oligomer has an average molecular weight of from 250 to 2,000,000 Daltons.

3. The composition of claim 1, wherein the amine-containing polymer or oligomer has an average molecular weight of from 500 to 10,000 Daltons.

4. The composition of claim 1, wherein the polyethyleneimine has a molar ratio of primary amines:secondary amines of from 1:1.25 to 1:0.75.

5. The composition of claim 1, wherein the polyethyleneimine has a molar ratio of primary amines:tertiary amines of from 1:0.90 to 1:0.40.

6. The composition of claim 1, wherein the polyethyleneimine has a molar ratio of primary amines:secondary amines:tertiary amines of 1:0.82:0.53, 1:0.91:0.64, or 1:0.94:0.67.

7. The composition of claim 1, wherein the weight ratio of the cloquintocet acid, or a salt thereof, to the amine-containing polymer or oligomer ranges from 1:1 to 5:1.

8. The composition of claim 1, wherein the pesticide includes an acetolactate synthase (ALS) inhibitor, an acetyl CoA carboxylase (ACCase) inhibitor, a 4-hydroxyphenylpyruvatedioxygenase (HPPD) inhibitor, a 4-aminopicolinic acid based herbicide, or combinations thereof.

9. The composition of claim 1, wherein the pesticide is a herbicide that includes pyroxsulam, clodinafop-propargyl, cyhalofop, fluazifop, haloxyfop, iodosulfuron, pinoxaden, pyrasulfotole, fenoxyprop, flucarbazone, flupyrsulfuron, halauxifen, halauxifen-methyl, mesosulfuron, quizalofop, thiencarbazone, or agriculturally acceptable salts or esters thereof, or combinations thereof.

10. The composition of claim 1, wherein the composition is an emulsifiable concentrate.

11. The composition of claim 1, wherein the composition is an aqueous spray solution or mixture.

12. A method of controlling undesirable vegetation comprising applying to the vegetation or an area adjacent the vegetation, or applying to the soil to prevent the emergence of the vegetation a herbicidally effective amount of the composition of claim 1.

13. The method of claim 12, wherein the undesirable vegetation is controlled in wheat, barley, triticale, rye, teff, oats, corn, sorghum, rice, sugar cane and pasture grasses, or combinations thereof.

14. The method of claim 12, wherein the undesirable vegetation is selected from the group consisting of wild oat, annual ryegrass, and combinations thereof.

15. A method for preparing a pesticidal composition comprising combining a pesticide and a safener complex comprising cloquintocet acid, or a salt thereof, and an amine-containing polymer or oligomer, wherein the weight ratio of the cloquintocet acid, or salt thereof, to the amine-containing polymer or oligomer ranges from 1:2 to 10:1, and wherein the amine-containing polymer or oligomer includes a branched, spherical polyethyleneimine.

* * * * *